Figure 1:
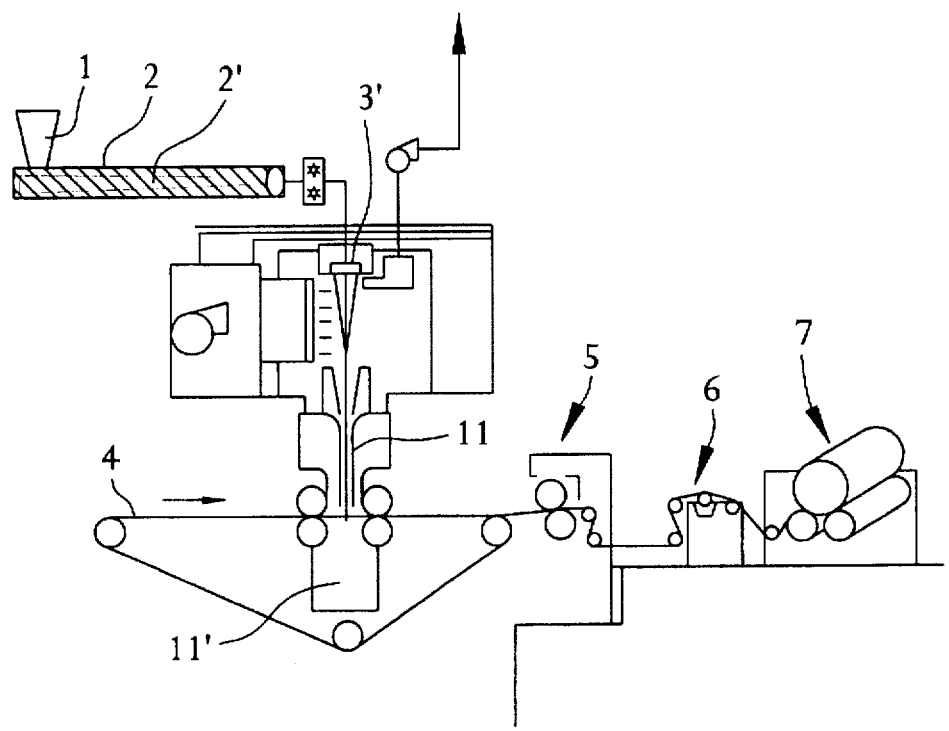

United States Patent [19]

Ehret et al.

[11] Patent Number: 5,783,504
[45] Date of Patent: Jul. 21, 1998

US005783504A

[54] NONWOVEN/FILM BIODEGRADABLE COMPOSITE STRUCTURE

[75] Inventors: Philippe Ehret, Fortschwihr; Kimmo Lahteenkorva, Kaysersberg, both of France

[73] Assignee: Fiberweb, Biesheim, France

[21] Appl. No.: 641,077

[22] Filed: Apr. 26, 1996

[30] Foreign Application Priority Data

Apr. 26, 1995 [FR] France .................................. 95 05186

[51] Int. Cl.⁶ ........................................................ B32B 27/34
[52] U.S. Cl. ........................... 442/395; 442/394; 442/400; 442/401; 442/402; 442/408
[58] Field of Search ................................. 442/394, 395, 442/400, 401, 402, 408

[56] References Cited

U.S. PATENT DOCUMENTS

| | | | |
|---|---|---|---|
| 5,097,005 | 3/1992 | Tietz | 528/272 |
| 5,171,308 | 12/1992 | Gallagher et al. | 604/372 |
| 5,300,358 | 4/1994 | Evers | 428/286 |
| 5,434,004 | 7/1995 | Ajioka et al. | 428/411.1 |
| 5,508,101 | 4/1996 | Patnode et al. | 428/286 |

FOREIGN PATENT DOCUMENTS 0569154  4/1993  European Pat. Off. .

OTHER PUBLICATIONS

Authors: R.K.Kulkarnt, Ph.D., K.C.Pani, M.D., C.Neuman, B.S., F.Leonard,PhD Title: "Polylactic Acid for Surgical Implants" Journal, vol. 93, pp. 839–843, Dated: Nov. 1966.

Authors: Duane E. Cutright, Joe D. Beasley, III, Bienvenido Perez Title: "Histologic Comparison of Polylactic and Polyglycolic Acid Sutures Journal, vol. 32, No. 1, pp. 165–173, Dated: Jul. 1971.

Authors: Reza-Ul Jalil, Ph.D. Title: "Biodegradable Poly (Lactic Acid) and Poly (Lactide-CO-Glycolide) Polymers in Sustained Drug Delivery", Article, pp. 2353–2367, Date: 1990.

*Primary Examiner*—Helen L. Pezzuto
*Attorney, Agent, or Firm*—Weiser and Associates P.C.

[57] ABSTRACT

Composite structure comprising one or more plies of nonwoven and one or more plies of film, these being manufactured from thermoplastics, wherein all the plies of nonwoven of which the structure is composed are totally manufactured from a polymer or a copolymer or a blend of polymers derived from lactic acid and wherein all the plies of film are totally manufactured from a polymer of the BAPE (biodegradable aliphatic polyester) type. The invention also relates to a process for manufacturing said composite structure.

Application: Diapers, sanitary napkins, protective garments, surgical drapes and masks in the medical field and certain products for absorption and filtration, protection of plants in agriculture and mulching.

10 Claims, 1 Drawing Sheet

NONWOVEN/FILM BIODEGRADABLE COMPOSITE STRUCTURE

The present invention relates to a composite structure comprising one or more plies of nonwoven which are combined with one or more polyester-based films.

The invention also relates to the process for manufacturing said composite structure and the method for combining the various plies of which it is composed.

Usually, the ply or plies of nonwoven are used as a support and are obtained by a spun-bond process designated by the abbreviation SB.

A film intended to provide both sealing and a barrier effect is added and/or another ply of SB nonwoven or of nonwoven obtained by a melt-blown process, designated by the abbreviation MB, is added.

Conventionally, said composite products are composed of polyolefins. The applications in which this type of composition is used are: diapers, sanitary napkins, protective garments, surgical drapes and masks in the medical field and certain products for absorption and filtration, protection of plants in agriculture and mulching.

Use-once and disposable products are manufactured with polymers which are often stable materials that do not degrade naturally.

The amount of waste continues to grow throughout the planet and the environment is becoming increasingly polluted. Spent products, such as films, nonwovens for hygiene (diapers, sanitary napkins, etc.), for medical applications (gowns, surgical drapes, etc.), and for agriculture (frost protection and mulching), constitute a large part of this solid waste.

The use of degradable polymers, in particular those which are biodegradable, constitute a large part of this solid waste.

These are mainly polymers derived from lactic acid (PLA), (Boehringer Ingelheim: RESOMER), from thermoplastic aliphatic polyester (Showa Highpolymer Co.: BIONOLLE ①, from polycaprolactone (PCL), (Union Carbide: TONE, Interox Chemicals: CAPA), from polyhydroxybutyrate/valerate (PHB/V), (Zeneca Bio Products: BIOPOL), from polyglycolic acid (PGA) and from many polymers and copolymers.

Application EP 93303000.9, "Biodegradable disposable diaper" filed by Showa Denko, relates to a totally biodegradable diaper using a biodegradable polyester nonwoven as a permeable surface web and as an impermeable rear ply. Application PCT/US92/00229, "Novel polyesters and their use in compostable products such as disposable diapers", filed by E. I. Dupont de Nemours and Company, relates to several types of use-once applications comprising fibers, films, foams, etc. based on novel bio-degradable polyesters.

These polymers are well known today in the medical field. They have been used as a raw material for sutures; reference may be made, for example, to: D. E. Cutright et al. in his treatise "Histologic comparison of polylactic and polyglycolic acid sutures", Oral Surg. 32, 165–173, 1971, for various types of implants (screws, rods and plates); "Polylactic acid for surgical implants" published in 1966 by R. K. Kulkarni et al., Arch. Surg. 93, 839–843; Eds et al. describes several systems for the controlled diffusion of an active principle in "Biodegradable polymers as drug delivery systems: manufacturing methodology, release control and targeting prospects", J. Bioactive Compatible Polymers 1990, 5, 315–342; as well as the Finnish company Bioscience Ltd which manufactures screws, nails, rods and plates (BIOFIX (①)), which are intended to consolidate bone fractures, based on polymers derived from lactic acid and from glycolic acid.

Polymers derived from lactic acid seem to be the most promising for replacing the stable polymers used hitherto in the composition of films and nonwovens. PLAs offer the possibility of obtaining mechanical and physico-chemical properties which are comparable to those of conventional polymers (U.S. Pat. Nos. 4,743,257 in 1988 and 4,968,317 in 1990).

However, totally biodegradable composite structures comprising plies of nonwoven and of films based on PLA are difficult to produce.

One aim of the invention is to solve this problem.

Indeed, it is very difficult to produce a fine PLA-based film.

Furthermore, given the relatively low recrystallization temperature (90°–110° C.) of PLA-based polymers, lamination or coating of nonwovens with PLA-based films poses problems. Films normally based on PLA also have a tendency to be rigid and are less easy to handle than films based on polyolefins, polyamides or polyesters.

The Applicant has therefore had the idea of combining plies of PLA-based nonwoven with films based on biodegradable aliphatic polyester, abbreviated to BAPE.

A BAPE-based film has mechanical properties similar to LDPE-based film, the elongation being especially superior to that of PLA-based film (BIONOLLE ①: >300%, PLA: 50–150%). It is also totally compatible with PLA-based nonwovens, which enables them to be calendered without any problem: it is not necessary to use adhesive coating, and extrusion coating is possible. The relatively low melting temperature (100°–200° C.) also enables the nonwoven to keep its structure during calendering. The combined use of these two polymers has an effect on the degradation properties of the composite: the duration of the degradation phase is less than that observed with plies comprising only PLA or BAPE. The BAPE-type polymer also has good air and oxygen permeability, superior to that of PET and LLDPE, which is paramount for applications in which air permeability is one of the specifications (protective garments, diaper rear web and several types of packages).

In addition to their degradable property, polymers derived from PLA are manufactured from renewable materials such as beet sugar or whey. Thus, the manufacture of these polymers does not at all disturb the natural balance (greenhouse effect) and does not use oil, which is a nonrenewable energy.

The invention has therefore solved the problems of the prior art by virtue of a composite structure comprising one or more plies of nonwoven and one or more plies of film, these being manufactured from thermoplastics, wherein all the plies of nonwoven of which it is composed are totally manufactured from a polymer or a copolymer or a blend of polymers derived from lactic acid and wherein all the plies of film are totally manufactured from a polymer of the BAPE (biodegradable aliphatic polyester) type.

Depending on the embodiment used, the polymer derived from lactic acid is a D-lactic acid or an L-lactic acid or a copolymer of DL-lactic acid or a mixture of L-lactic acid and D-lactic acid.

Preferably, the polymer, copolymer or polymer blend has an average molecular weight of between 10,000 and 1,000,000.

Furthermore, the polymer used for the ply of film is preferably BIONOLLE. Said polymer used for the ply of film may be produced via a chemical polymerization reaction between glycols and aliphatic dicarboxylic acids and others, for example polyethylene succinate (PESU).

According to preferred embodiments, all the plies of nonwovens of which the invention is composed are manufactured by a process chosen from the group (SB, dry route, MB) and/or all the plies of film are produced by extrusion.

All the plies of nonwovens are bonded together and bonded to the plies of film by thermal bonding, needle punching, water jets, overblowing or chemical bonding agent.

All these plies may be bonded together on line or separately.

The invention will be better understood with the aid of the description hereinbelow, given with reference to the following appended figures:

FIG. 1: a diagram of a spinning installation of the spun-bond or SB type; and

Figure 2:
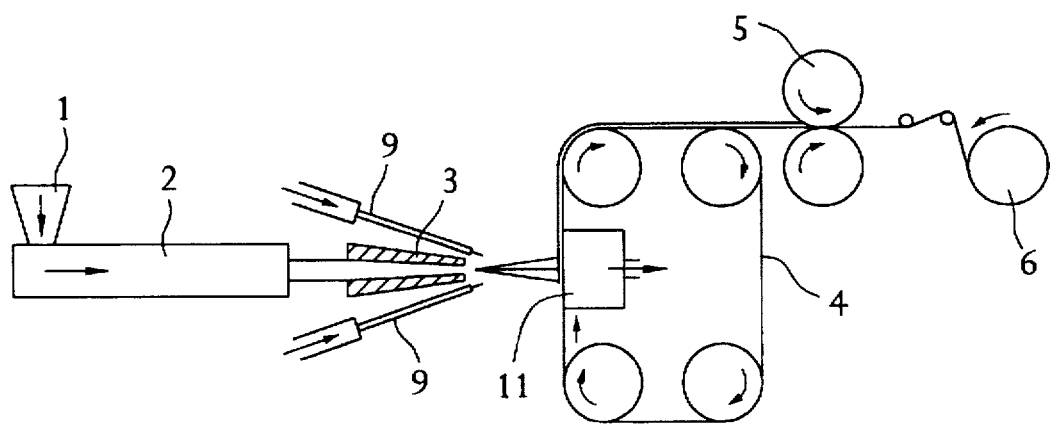

FIG. 2: a diagram of an installation for manufacturing a web using a process of the melt-blown or MB type.

The present invention relates to a biodegradable composite structure comprising one or more plies of nonwoven based on polymer derived from polylactic acid (PLA), these being combined with one or more films based on aliphatic polyester (BAPE) having a chemical structure identical to that of BIONOLLE ①:

$$\sim\!|\!-\!O\!-\!(CH_2)_a\!-\!O\!-\!\underset{O}{\overset{\parallel}{C}}\!-\!(CH_2)_b\!-\!\underset{O}{\overset{\parallel}{C}}\!-\!|\!\sim$$

It is produced by a chemical reaction of glycols with aliphatic dicarboxylic acids and others. For example, it may be polyethylene succinate (PESU (a=2)) and polybutylene succinate (PBSU (b=4)). It has a density lying between 1.2 and 1.3 g/cm$^3$. It is soluble in water, alcohol, acetone, etc.

Each ply possesses mechanical properties—barrier effect, absorption, filtration and thermal insulation—which may be adapted to each application by selecting the appropriate composition of PLA-based nonwovens and BAPE-based films.

The PLA-based polymers are composed of pure poly(L-lactide) (PLLA), pure poly(D-lactide) (PDLA), copolymers of poly(DL-lactide) whose ratio varies from 0% to 100%, as well as blends of the polymers mentioned.

The number average molecular weight determined by gel permeation chromatography of the polymer may vary from 10,000 to 1,000,000, preferably from 40,000 to 600,000. As significant degradation occurs during melting, the molecular weight must not be less than this.

The molecular weight of a polymer derived from BAPE could lie between 10,000 and 600,000 or preferably from 20,000 to 300,000.

The raw materials (polymers derived from PLA and from BAPE) used in this invention may contain a plasticizer in proportions of from 0.1 to 15% and/or from 0.1 to 20% of lactic monomer and/or from 0.01 to 5% of various types of stabilizers, pigments and other colorants.

Each ply of said multiply composite product may be produced by using various compositions of PLA-based raw materials and various additives. Each ply of film is produced from polymer derived from BAPE.

Said composite is composed of at least one ply. Each of these plies is either a web of nonwoven or a film, so that the composite includes at least one nonwoven. Each ply is intended for a specific use. In the case of a surgical drape, for example, said composite includes a ply of nonwoven having absorption and comfort properties, and a ply of film having a barrier (viral barrier) effect. Said compositions, particularly MB and SB compositions, may also be used in sanitary napkins (U.S. Pat. No. 5,478,069 of 1986, using a composite based on polyolefins) or sterilization wraps (U.S. Pat. No. 4,766,029 of 1988, using an SB+MB+SB three-ply laminate).

In the present invention, the web of nonwoven is a material similar to a woven fabric, but manufactured without weaving or knitting, having a structure of oriented fibers. The fibers may either be continuous or have a length varying from 5 mm to 500 mm. Preferably, the fiber gage is from 0.1 to 100 µm.

The web(s) may be bonded or not bonded. Bonding may be performed by needle punching, water jets, chemical bonding agent or thermal bonding.

a) Manufacture of the nonwoven

Various SB-type processes for manufacturing webs of nonwovens, such as the Lurgi and S-Tex processes, and the MB (melt-blown) process, exist.

The SB web provides the composite structure with good mechanical properties (strength, elongation and pliancy). It may also be used for absorption and filtration. In some applications where it constitutes the surface ply, it provides softness and comfort.

In this process, the polymer is melted and extruded by means of a single-screw or twin-screw extruder, at a temperature preferably lying between 140° and 280° C., and is conveyed to a spinning pump before passing through a filter up to a spinneret having holes varying from 0.2 to 2.0 mm and preferably from 0.4 to 1.0 mm. The polymer is spun through the spinneret as far as the cooling and drawing installation. The cooling may be performed by means of chilled air, at a temperature varying preferably between 0° and 40° C. and the rate varying from 0.1 to 5 m/s, and the drawing may be performed by air which is sucked or blown through the drawing system. The drawing system may have one slit or may be formed by a series of tubes or slits. The speed of the drawing air is preferably between 10 and 400 m/s. In the drawing system, the fibers obtained have a decreasing diameter and an oriented structure. The draw ratio is generally from 1.1× to 20×, preferably from 2× to 15×. In the SB ply, the linear density of the fibers is preferably between 0.5 and 20 dtex, more particularly from 1 to 10 dtex.

The spinning system is followed by a laydown system which lays the fibers down randomly on the belt. The belt conveys the web of fibers to a calender heated to a temperature varying preferably from 40° to 160° C., more particularly from 60° to 110° C. Before calendering, the other webs are combined in order to form the composite, for example another SB web, an MB web or both of them, and/or a ply of film.

The basis weight may be adjusted depending on the speed. It is generally between 5 and 200 g/m$^2$, depending on the application.

The diagram in FIG. 1 is a representation of the SB (i.e. S-Tex) process: 1) the hopper for raw material, 2) the extruder, 2$a'$) the screw, 3') the spinneret, 4) the belt, 5) the calender, 6) the system for guiding the web and for adjusting the wind-up tension, 7) the winding, 9) the system for cooling the fibers, 11) the drawing slit, 11') the suction for drawing.

The web of said composite structure is intended to provide properties such as absorption, filtration and/or thermal insulation, softness and comfort. It also enables the permeability of the composite to be adapted.

The MB process also comprises an extruder intended to melt the polymer. The temperatures are preferably between 150° C. and 280° C. The polymer is conveyed from the extruder to the spinneret. The spinneret has only a single row of holes. The holes have a diameter of from 0.2 to 2 mm.

A flow of air from both sides of the row of holes blows the polymer in fiber form onto the moving web. The fiber linear density is from 0.05 to 2 dtex. The basis weight of the MB web is adjusted as a function of the speed of the belt.

The MB web may be deposited directly on the SB web. This process is called overblowing. In this process, the SB system is installed before the MB system, both being installed before the calender. The two webs are thermally bonded by calendering.

The diagram in FIG. 2 represents the MB process: 1) hopper for raw material, 2) extruder, 3) spinneret, 4) forming belt, 5) calender, 6) winder, 9) blowing, 11) suction.

The ply of film of said composite structure is intended to provide properties such as liquid-barrier properties and good drapability. However, the film may be porous (U.S. Pat. No. 5,208,098 of 1993) and in this case it is permeable and absorbent.

b) Manufacture of the film

The BAPE film is deposited on the composite structure by extrusion. The temperature of the extruder is from 150° C. to 220° C. and the slot of the die is from 0.2 to 2 mm. The ply of film may be extruded separately and bonded to the composite by calendering, it being possible in this case to combine with it only a nonwoven structure calendered beforehand, or the extruded film may be used to bond 25 separate nonwoven plies. The thickness of the film or films of said composite structure is preferably from 0.001 to 1.0 mm.

Use of the BAPE-type polymer for the manufacture of a film in said composite structure provides a non-negligible advantage: the melting temperature of this polymer is from 40° to 60° C. lower than that of the PLA-based polymer, which allows laminating, calendering or extrusion coating to be carried out at lower temperatures, so that the nonwoven retains its strength and its softness.

c) Manufacture of the composite according to the invention

Several ways of manufacturing said composite structure according to the invention exist, for example:

1. The composite nonwoven is bonded by thermal bonding, needle punching, water jets, overblowing (MB) or chemical bonding agent, and the films are combined with this composition by lamination or calendering (FIG. 3: 1) composite nonwoven, 2) film, calendering).

2. The composite nonwoven bonded by thermal bonding, needle punching, water jets, overblowing (MB) or chemical bonding agent is combined with the film(s) by the extrusion-coating (FIG. 4: 1) bonded nonwoven, 3) extrusion die, 4) film).

3. The nonwoven is bonded by the extrusion-coating of a film. In the case of two or more plies of nonwoven, the film is extruded between the plies so as to bond them and, in the case of a single ply of nonwoven, this ply is combined with the film by the extrusion-coating (FIG. 5: 1–2) nonwoven, 3) extrusion die, 4) film).

A BAPE-based film combined with a PLA-based nonwoven degrades more rapidly, during compositing or during hydrolysis, than a composite nonwoven based only on PLA. Usually, a PLA-based composite structure comprising a 30 g/m² nonwoven combined with a 10 g/m² film degrades in the space of 6 to 8 weeks whereas, in the case of a composite based on PLA and BAPE, degradation takes place in less than a month. This composite also promotes the growth of bacteria and molds which allow more rapid degradation with production of water and $CO_2$.

Described hereinbelow, by way of nonlimiting examples, are two nonwoven structures in accordance with the invention.

EXAMPLE 1

Composite structure for agriculture

The composite structure intended for use in agriculture includes a PLA-based SB web and a ply of BAPE-based film. The structure may be manufactured by the extrusion-coating of a ply of film on the SB web or by laminating these two plies together by thermal bonding. A black colorant (carbon black 0.5–1.5% [lacuna] suitable for mulching (U.S. Pat. No. 3,580,196 of 1971) using a nondegradable plastic sheet).

In the mulching application, the SB web provides the strength and the film provides impermeability. In addition, when the SB ply forms the outer face, the latter dries more rapidly after rain, enabling fruit (for example, strawberries) and vegetables (for example, lettuces) to be kept in good condition. Moreover, the impermeable film prevents the soil from drying out. The black color forms a sun screen and thus prevents weeds from growing.

In short, in this case, biodegradability offers the following advantages: the mulching product may be left in place and will degrade with time (a function which can vary from 2 to 36 months) and it may also be removed and buried, or intended for composting with degradation over several weeks.

In said composite structure, the SB web preferably has a weight of from 15 to 75 g/m² and the thickness of the film is from 0.01 to 0.10 mm depending on the specifications in terms of mechanical properties and lifetime. For example, the mulching product containing 1% by weight of carbon black, having a weight of 50 g/m² for the SB web and a film thickness of 0.025 mm, has the following properties:

elongation at break: 55–75% machine-direction strength: 110–160 N/m².

The lifetime may be varied by using a UV stabilizer.

EXAMPLE 2

Laminated composite structure for hygiene application

This composite structure is composed of:

a PLA-based nonwoven having a weight of 20 g/m², a linear density of 1.9 dtex, a strength of 35 N/5 cm in the machine direction and 10 N/5 cm in the transverse direction, and an elongation of 40% in the machine direction and 50% in the transverse direction. The average molecular weight is 100,000 and the percentage of monomer is 0.5%;

a BIONOLLES ①film having a thickness of 8 μm ($\cong$10 g/m²), a tensile strength of 300 kg/cm² and an elongation of 300%.

These two plies are laminated together to form a composite structure offering the following properties:

strength: 50/5 cm in the machine direction and 25 N/cm in the opposite direction;

elongation: 40% in the machine direction and 55% in the transverse direction;

softness and textile feel;

air and water permeability;

total degradation in compositing in 5 weeks.

This composite can be used either as an impermeable face of a hygiene article (for example a rear face of diapers) or as a leakproof barrier in diapers for babies and for the incontinent.

In general, the composite structure according to the invention is characterized in that all the plies of nonwoven and of film of which it is composed each offer specific properties depending on the manufacturing process, the method of bonding and the type of polymer which are selected.

Finally, it may be adapted to a product intended for hygiene (diapers, incontinence, feminine hygiene, etc.), for use in agriculture (mulching and surface sheeting) or in the medical sector (surgical drapes and gowns).

We claim:

1. A composite structure comprising at least one ply of nonwoven of thermoplastic homopolymer, copolymer or blend of homopolymer or copolymer of lactic acid and at least one ply of film of thermoplastic homopolymer of biodegradable aliphatic polyester.

2. The composite structure of claim 1, wherein said lactic acid is selected from the group consisting of D-lactic acid and L-lactic acid.

3. The composite structure of claim 1, wherein said lactic acid is DL-lactic acid.

4. The composite structure of claim 1, wherein said polymer is a of mixture of L-lactic acid and D-lactic acid.

5. The composite structure of claim 1, wherein the homopolymer, copolymer or blend of homopolymer or copolymer of lactic acid has a number average molecular weight determined by gel permeation chromatography of between 10,000 and 1,000,000.

6. The composite structure of claim 1 wherein the biodegradable aliphatic polyester-based polymer has the chemical structure

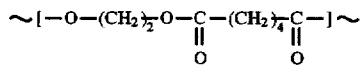

7. The composite structure of claim 1 wherein the biodegradable aliphatic polyester based polymer is produced by a chemical polymerization reaction between glycols and dicarboxylic aliphatic acids.

8. The composite structure of claim 1, wherein the thickness of the filaments of each ply of nonwoven of which it is composed is between 0.1 and 100 μm.

9. The composite structure of claim 1, wherein the thickness of each film of which it is composed is between 0.0001 and 1 mm.

10. An agricultural mulch product comprising a composite structure of claim 1.

* * * * *